United States Patent [19]

Henderson et al.

[11] Patent Number: 5,476,000
[45] Date of Patent: Dec. 19, 1995

[54] RETENTION TIME STABILITY IN A GAS CHROMATOGRAPHIC APPARATUS

[75] Inventors: Robert Henderson, Avondale; Edwin Wikfors, Landenberg, both of Pa.

[73] Assignee: Hewlett-Packard Company, Palo Alto, Calif.

[21] Appl. No.: 220,432

[22] Filed: Mar. 31, 1994

[51] Int. Cl.⁶ .................................................. G01N 30/32
[52] U.S. Cl. .......................... 73/23.27; 73/23.24; 95/15; 95/22
[58] Field of Search ............... 73/23.24, 23.27, 73/23.42, 23.22, 23.36; 55/270; 95/15, 19, 22, 23, 82; 96/102

[56] References Cited

U.S. PATENT DOCUMENTS

| | | | |
|---|---|---|---|
| 2,964,938 | 12/1960 | Fuller | 73/23.27 |
| 3,104,541 | 9/1963 | Noebels et al. | 73/23.27 |
| 3,240,052 | 3/1966 | Reinecke et al. | 73/23.27 |
| 3,283,563 | 11/1966 | Turner et al. | 73/23.27 |
| 4,141,237 | 2/1979 | DeFord et al. | 73/23.27 |
| 4,196,612 | 4/1980 | Clardy et al. | 73/23.27 |
| 4,379,402 | 4/1983 | Harmann, III | 73/23.21 |
| 4,512,181 | 4/1985 | Ayers et al. | 73/23.27 |
| 4,927,434 | 5/1990 | Cordes et al. | 95/15 |
| 4,994,096 | 2/1991 | Klein et al. | 95/15 |
| 5,108,466 | 4/1992 | Klein et al. | 95/1 |
| 5,163,979 | 11/1992 | Patrick et al. | 95/19 |
| 5,339,673 | 8/1994 | Nakagawa et al. | 73/23.36 |
| 5,379,629 | 1/1995 | Müller | 73/23.27 |

OTHER PUBLICATIONS

Thompson, M. Q., "Chapter 2—Pressure/Flow Relationship in Capillary Gas Chromatography" in: Stafford, S. S. "Electronic Pressure Control in Gas Chromatography". (Hewlett–Packard Co., Sep. 1993) pp. 25–42.

Primary Examiner—Thomas P. Noland
Assistant Examiner—Michael J. Brock
Attorney, Agent, or Firm—Mark Z. Dudley

[57] ABSTRACT

The effect of barometric pressure variation on the retention time stability of a chromatographic analytical system is compensated by active control of the amount of fluid flow by way of a fluid flow controller, preferably in the form of an electronic pressure control system. Control signals are derived by: receiving data representative of a desired operating condition parameter, such as column inlet pressure; sensing actual operating condition parameters such as inlet pressure $p_i$ and barometric pressure $p_{atm}$; determining a desired average linear velocity of the fluid flow according to the desired operating system parameter; determining an actual average linear velocity of the fluid flow according to the sensed plurality of actual operating condition parameters; and controlling, as a function of a predetermined relationship of the desired average linear velocity to the actual average linear velocity, the amount of fluid flow to cause the actual average linear velocity to substantially equal the desired average linear velocity.

29 Claims, 6 Drawing Sheets

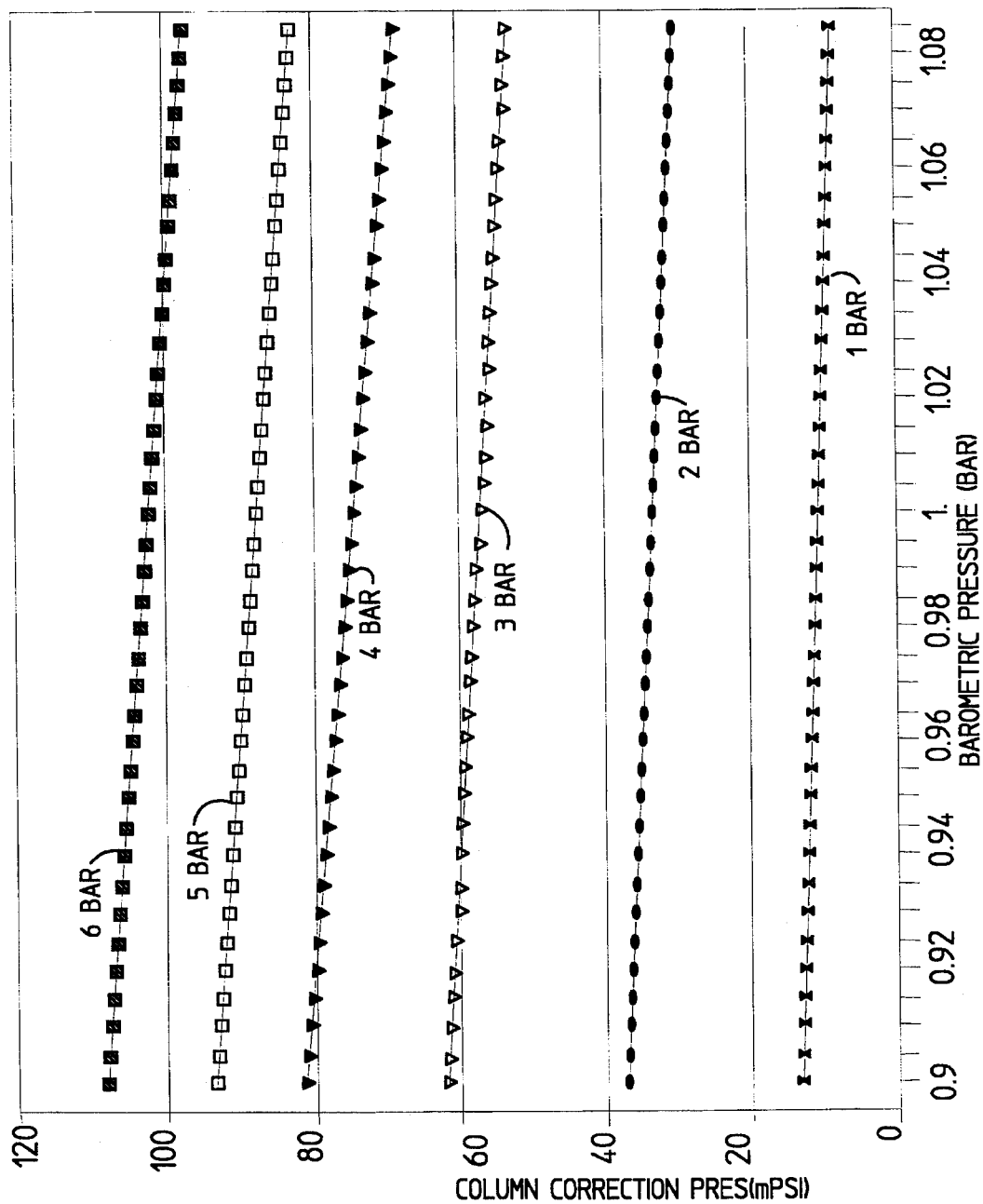

RETENTION TIME STABILITY IN A GAS CHROMATOGRAPHIC APPARATUS

FIELD OF THE INVENTION

The present invention relates to chromatographic analysis systems and, more particularly, to an apparatus and method for improved control of the fluid flow through a chromatographic column.

BACKGROUND OF THE INVENTION

Modern gas chromatographic analytical systems are particularly susceptible to performance variations due to variations in the ambient conditions in which the analytical system is operated. For example, the outlet pressure of the chromatographic column is substantially equal to the ambient atmospheric pressure, which is an uncontrollable variable. FIG. 1 shows one typical variation of ambient atmospheric (hereinafter barometric) pressure recorded over 17 days; pressure variations were found to vary over a range of approximately 4%. Additionally, analytical methods and processes are sometimes developed or performed on chromatographic systems in centrally-located analytical labs, and then transferred to other locations for continued development, research, application to production line processing, or field monitoring. Any barometric pressure differences between such locations will result in some variation in the performance of the chromatographic systems at the respective locations.

Proper analytical test methods therefore include frequent recalibration so as to correct for any systematic errors or shifts due to barometric pressure changes. Further, some conventional chromatographic equipment incorporates a form of pressure control or mass flow control for correcting an error due to ambient conditions.

In U.S. Pat. No. 4,141,237, issued to DeFord et al., a method and apparatus is disclosed wherein errors in a chromatographic analysis caused by changes in ambient atmospheric pressure are said to be corrected. In such an analysis, the output signal from a chromatograph is summed with the output signal from a pressure transducer. The output signal from the pressure transducer varies with changes in the atmospheric pressure from a reference pressure and is calibrated in such a manner as to provide a corrected chromatographic analyzer output signal when it is summed with the output signal from the chromatograph. In this manner pressure compensation is said to be provided where normalization of the chromatographic analyzer output signal is not possible or is undesirable.

In U.S. Pat. No. 4,512,181 issued to Ayers et al., errors in a chromatographic analysis caused by barometric pressure variations are said to be corrected by dividing an actual measured analysis value (Cm) by a correction factor that is calculated according to the actual atmospheric pressure at the time the measurement is made (Pa), the atmospheric pressure at which the chromatographic analyzer system was calibrated (Pc), and the slope of a plot of Cm/Ca as a function of Pa/Pc where Ca is the magnitude that Cm would have if errors were not introduced by changes in barometric pressure.

In U.S. Pat. No. 4,196,612, issued to Clardy et al., an absolute back pressure regulator is said to provide a constant reference pressure for a chromatographic analyzer system by supplying all the gaseous streams of the chromatographic analyzer system (which are normally vented to the atmosphere) to the input side of the absolute back pressure regulator. These gaseous streams include the sample vent for the chromatographic analyzer sample valve, the sample vent for the chromatographic analyzer sample detector, and the carrier vent for the chromatographic analyzer reference detector. The carrier gas pressure regulator is also said to be referenced to the constant pressure supplied by the absolute back pressure regulator instead of to atmospheric pressure. However, the column effluent and solvent venting apparently are made to pass through fluid lines to the absolute back pressure regulator. Such an approach requires another flow path that is subject to pressure leaks and other problems which may cause errors in pressure control or, another valve and pressure sensor may be needed in the split line, which adds undesirable complexity. Further, a back pressure regulator and the fluid lines that serve such a regulator may be subject to occlusion by deposits of compounds in the fluid steam, or to corrosion from the detector effluent from destructive detectors (e.g., a flame ionization detector or FID). The disclosed approach also can be subject to silent failure, wherein a failure in the reference pressure pneumatics can result in the loss of the desired control signal if, for example, the absolute pressure regulator were to become stuck open. Severe failure of the reference pressure pneumatics may occur if the same regulator were to become closed.

Accordingly, a need exists for a chromatographic system wherein the effect of barometric pressure on the passage of the carrier fluid through the chromatographic column is more accurately and reliably controlled.

SUMMARY OF THE INVENTION

Retention time stability in a chromatographic system is a desirable characteristic that determines the ability of the system to properly identify closely eluting components or to have a component be identified within a desired 'identification window' of time. Retention time is considered herein as a function of the average linear velocity of the fluid, which in turn is a function of operating condition parameters such as the column dimensions or temperature, the inlet or outlet pressure, and the gas viscosity. Retention time stability is then achieved if the actual average linear velocity of the fluid is maintained at a selected level. If the characteristics of a given sample compound, column, and carrier fluid are known, then the retention time may be primarily stabilized by improved control of average linear velocity of the carrier fluid in the column.

Accordingly, the present invention provides a method and apparatus for performing a chromatographic analysis of a fluid, wherein fluid flow of the fluid is provided in a separation column having an outlet subject to a barometric pressure $p_{atm}$. A plurality of actual operating condition parameters, including barometric pressure $p_{atm}$, are sensed. Information representative of a desired operating condition parameter is received, and a desired average linear velocity of the fluid flow is determined according to the desired operating system parameter. In response to a variation in the sensed barometric pressure, an adjustment to the fluid flow is determined such that the adjustment will cause the actual average linear velocity to substantially equal the desired average linear velocity.

In one preferred embodiment of the invention, a control signal representative of the fluid flow adjustment is used to adjust the fluid flow at the column inlet to effect the desired average linear velocity of the fluid flow in the column.

In another preferred embodiment, and according to a particular feature of present invention, the difference in actual barometric pressure from standard conditions is measured, and adjustments are made to the column inlet pressure to compensate for the effect of barometric changes.

The method and apparatus taught herein affords improved stability of the retention time of a chromatographic analytical system even while the system is influenced by variations in barometric pressure $p_{atm}$. The preferred embodiments of the invention do not require the full functioning of an absolute pressure controller for normal operation, or the additional pneumatic plumbing, as found in the prior art. A failure of the sensors in the preferred embodiment is a detectable condition; e.g., a barometric pressure sensor failure will result only in the loss of the barometric pressure compensation, rather than a silent failure of the pressure control system.

BRIEF DESCRIPTION OF THE DRAWINGS

FIG. 6 is a graphical representation of column head pressure correction values that were determined according to the present invention to maintain a constant average linear velocity of a column fluid flow in a typical column.

DETAILED DESCRIPTION OF THE PREFERRED EMBODIMENTS

Figure 1:
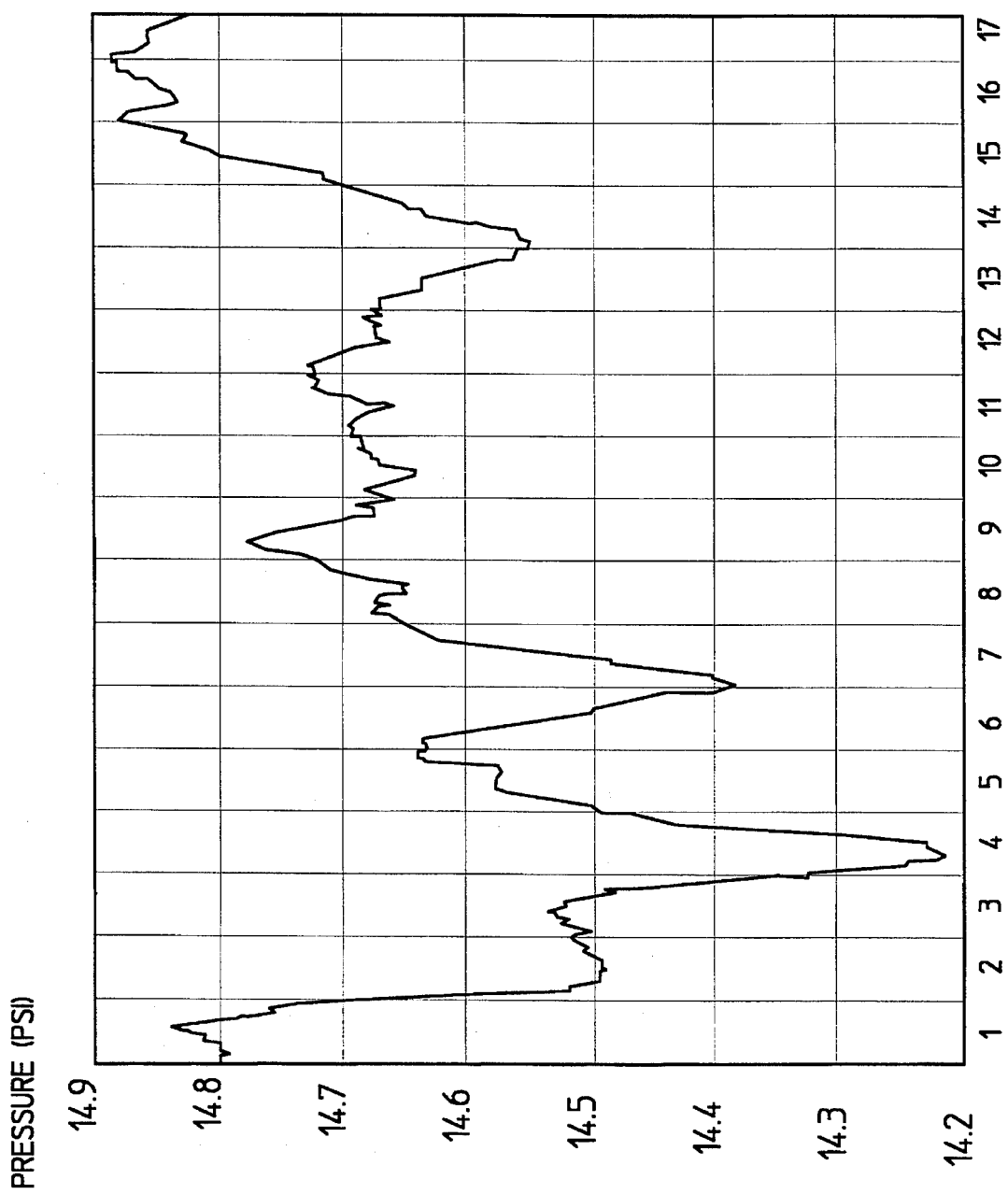
FIG. 1 is a graphical representation of the range of variation in barometric pressure as measured by the National Weather Service at the Wilmington, Del. airport in March 1991 over a period of seventeen days.

The apparatus and methods of the present invention may be employed to improve the control of a variety of compressible fluids in an analytical chromatographic system. Such fluids are intended to include gases, liquids, multiple component gases and liquids, and mixtures thereof capable of regulated flow. Gases are the preferred fluids according to the practice of the present invention, and therefore the following description of the invention will be directed to a gas chromatographic analytical system. However, it should be understood that the teachings herein are applicable to analysis of other compressible fluids.

In analytical chemistry, liquid chromatography (LC) and gas chromatography (GC) techniques have become important tools in the identification of chemical sample components. The basic mechanism underlying chromatographic analysis is the separation of a sample chemical mixture into individual components by transporting the mixture in a carrier fluid through a specially prepared separation column having a retentive media therein. The carrier fluid is referred to as the mobile phase and the retentive media is referred to as the stationary phase. The principal difference between liquid and gas chromatography is that the mobile phase is either a liquid or a gas, respectively. The analytical choice between liquid and gas chromatography techniques is largely dependent on the molecular weight of the components to be analyzed. Liquid chromatography devices are capable of analyzing much heavier compounds than gas chromatography devices. However, gas chromatography detection techniques are more sensitive and therefore are generally preferred.

In a gas chromatographic analysis, an inert carrier gas is passed through a temperature-controlled column which contains a stationary phase in the form of porous sorptive media, or through a hollow capillary tube having an inner diameter in the range of few hundred microns coated with the stationary phase. A sample of the subject mixture is injected into the carrier gas stream and passed through the column. As the subject mixture passes through the column, it separates into its various components. Separation is due primarily to differences in the partial pressures of each sample component in the stationary phase versus the mobile phase. These differences are a function of the temperature within the column. A detector, positioned at the outlet end of the column, detects each of the separated components contained in the carrier fluid as they exit the column.

Basic techniques for the control of the flow of a fluid in a chromatographic analytical system are known to those skilled in the art. For details of an electronic pressure control system, one may consult, for example, Klein, et al., U.S. Pat. No. 4,994,096 and U.S. Pat. No. 5,108,466, the disclosures of which are incorporated herein by reference. Klein et al. also disclose a technique for subjecting at least a portion of the chromatographic column to a temperature profile. Klein et al. also disclose electronic pressure control of fluids in "CGC Using a Programmable Electronic Pressure Controller," *J. High Resolution Chromatography* 13:361, May 1990. Larson, J. R. et al., in *Journal of Chromatography*; 1987, 405, at 163–168 discuss a continuous flow programming technique for process capillary gas chromatography. Earlier control systems may be found in, for example, Scott, R. P. W., "New Horizons in Column Performance", *Gas Chromatography*, 1964; Costa Neto, C., et al., *Journal of Chromatography*, 1964, 15; and Zlatkis, A., *Journal of Gas Chromatography*, March 1965, 75–81.

Figure 2:
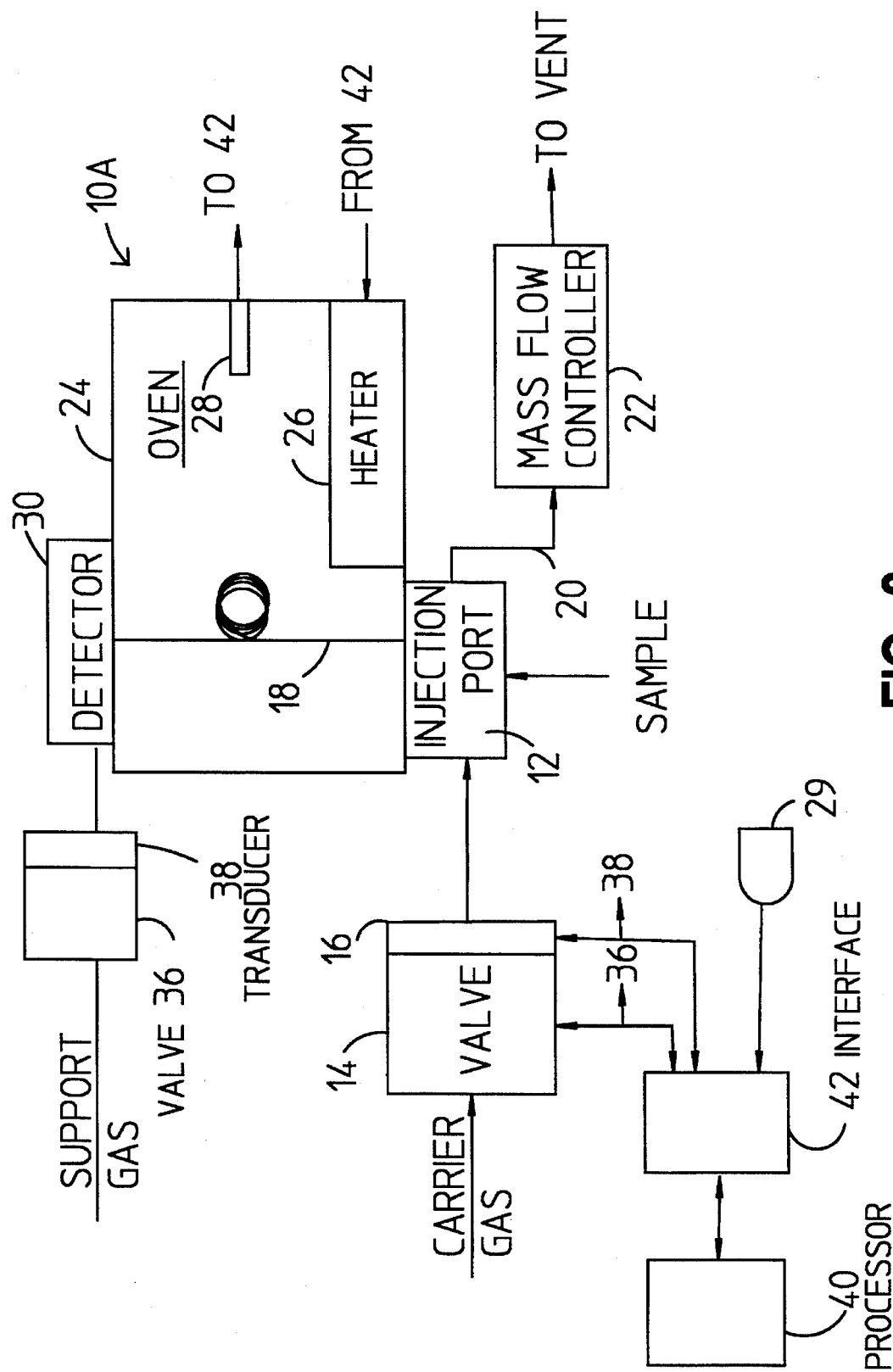
FIG. 2 is a simplified schematic representation of a preferred embodiment of a gas chromatographic analysis system constructed according to the teachings of the present invention.
Figure 3:
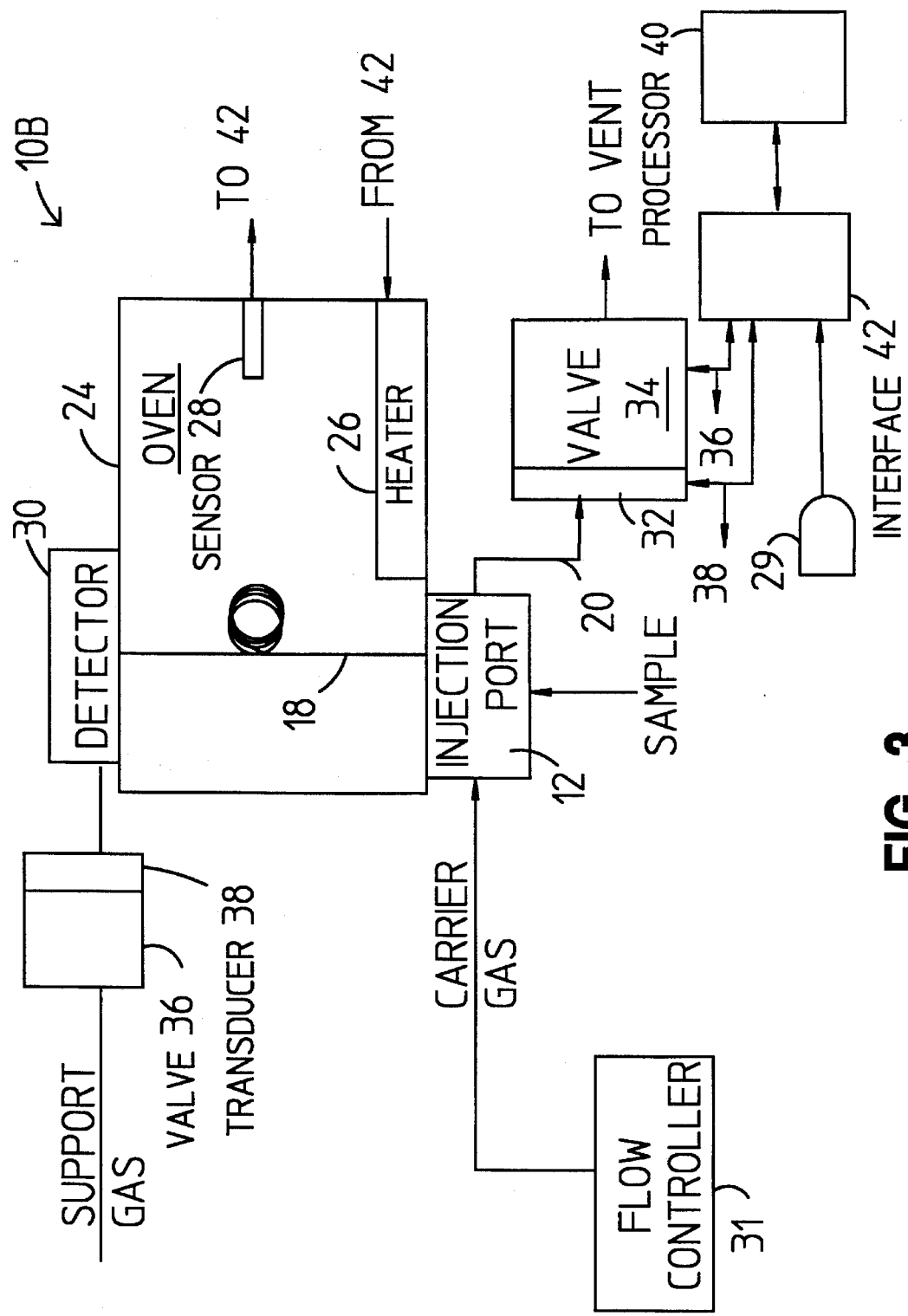
FIG. 3 is a simplified schematic representation of another preferred embodiment of a gas chromatographic analysis system constructed according to the teachings of the present invention.

Accordingly, and as illustrated in FIGS. 2 and 3, the present invention is directed to an apparatus and method for improved control of the amount of fluid flow through a chromatographic column. The preferred fluid flow control is preferably accomplished by an electronic pressure regulated system which, as shown in FIGS. 2 and 3, can be characterized by the type of pressure feedback used: either forward pressure regulation, or back pressure regulation.

As will be seen with respect to FIG. 2, a forward pressure regulator receives feedback to control pressure downstream from the controlling valve. If the downstream pressure momentarily drops below setpoint, a feedback signal (preferably an electronic control signal) causes the flow controller to pass more fluid. Similarly, when the pressure rises above setpoint, the valve will close further. As will be seen with respect to FIG. 3, a back pressure regulator controls pressure upstream of the flow controller. If the upstream pressure momentarily drops below setpoint, for example, a feedback signal causes the controller to reduce flow.

The preferred embodiment illustrated in FIG. 2 is a gas chromatographic analytical system (10A) arranged in a forward pressure regulated configuration, which is amenable for use with so-called cool on-column, packed, and large bore (i.e., about 530 micron) direct techniques. In order to perform a chromatographic separation of a given sample compound, the sample is injected into a fluid, preferably in the form of a pressurized carrier gas, by means of an injection port (12). The carrier gas is supplied to the injection port (12) from a source through a fluid flow controller preferably in the form of a valve (14). It will be appreciated by those skilled in the art that in accordance with the teachings hereinafter, the operation of the flow controller serves to control the pressure and/or the volumetric flow rate of the carrier gas in the GC system. The carrier gas may comprise one or more component gasses-such as, for example, hydrogen, nitrogen, or helium-depending upon the particular chromatographic separation to be performed. A mixture of argon and 4% methane is common carrier gas used with electron capture detectors.

A plurality of transducers generate sense signals representative of actual operating condition parameters for use in the control system to be described hereinbelow. Preferably, one sensed parameter is the inlet pressure of the carrier gas provided to the injection port (12). This inlet pressure sense signal is provided by an inlet pressure sensor (16) to an interface (42). The signal is then provided to a processor (40), which in turn provides a control signal to the valve (14). Operation of the valve (14) then regulates the pressure of the carrier gas in response to the control signal. The particular design of valve (14) is not critical to the present invention, and a Model Number 001–1014 pressure valve sold by Porter Instrument Company, Inc. of Hatfield, Pa. is suitable. One suitable sensor (16) is 1210-A100G3L transducer sold by I.C. Sensors of Milpitas, Calif.

The injection port (12) provides a portion of the sample/carrier gas mixture to a separation column (18), with the remainder passing through a non-analyzed output (20). The flow exiting the output is known as the septum purge flow. By maintaining a relatively constant purge flow through a downstream-referenced flow controller (22), it is possible to minimize "false" peaks from the injection port septum (not shown) and also minimize air diffusion into the column (18). The column (18) is positioned within a temperature-controlled thermal chamber, or oven (24). The oven (24) preferably includes a heating unit (26) and a temperature sensor (28). In order to ensure that the temperature within the oven (24) is at a desired level, another transducer in the form of a temperature sensor (28) generates another sense signal representative of an actual operating condition parameter, that is, the temperature in the oven (24), which signal is also provided to interface 42 and the processor (40). The heating unit (26) maintains controlled temperature in the oven (24) in response to the control signal generated by the processor (40). The carrier gas/sample combination passing through the column (18) is thereby exposed to a temperature profile resulting from the operation of the heater (26) within the oven (24). Typically, the temperature in the oven (24) is controlled according to a selected program so that the sample will separate into its components.

As the carrier gas (containing the sample) exits the column (18), the presence of one or more sample constituent components is detected by a detector (30). The detector (30) can be any of the GC detectors known in the art, so long as it is capable of determining at least one physicochemical property of the carrier fluid which exits the column (18). Those skilled in the art will appreciate that the term "detector" include a wide variety of useful chromatographic detectors, such as the flame ionization detector (FID), photoionization detector (PID), nitrogen phosphorous detector (NPD), flame photometric detector (FPD), thermal conductivity detector (TCD), atomic emission detector (AED), electrolytic conductivity detector (ELCD), and electron capture detector (ECD). Mass spectral detectors and infrared spectral detectors are also known.

As will be described below, another transducer in the form of an absolute ambient pressure sensor (29) provides a signal representative of the ambient barometric pressure $p_{atm}$ at the outlet to the interface (42) and processor (40). The sense signal may be considered for the purposes of the invention to also represent the column outlet pressure $p_o$ referenced to absolute pressure. A suitable absolute pressure transducer (29) may be constructed with a diaphragm mounted across a volume that contains a vacuum, whereby the transducer (16, 32) provides a signal representative of the pressure differential across the diaphragm. A commercial version of such a transducer, available from IC Sensors, may be in the form of a 5 psi sensor electrically trimmed to produce its null output at 10 psia and full scale at 15 psia.

Without departing from the principles of the present invention, the pressure of the carrier gas can also be regulated according to a back pressure mode, wherein the valve (14) regulates pressure sensed in the region located upstream from the valve. For example, the chromatographic analytical system (10B) depicted in FIG. 3 is arranged in a back pressure regulated design suitable for so-called split injections. In a split injection, a portion of the sample to be analyzed is injected onto the column (18) while the remainder of the sample is "split" off the column (18) and vented. As shown in FIG. 3, the carrier gas is provided directly to the injection port (12) from a flow controller (31). The pressure of the carrier gas is determined by the pressure transducer (32) which senses the pressure of the carrier gas/sample combination in the non-analyzed output (20). The pressure of the carrier gas exiting the injection port (12) is controlled by a valve (34) in response to an appropriate signal from processor (40). The ratio between that portion of the sample/carrier gas provided to the output (20) and the remainder provided to the column (18) is known as the split ratio. The split ratio regulates the amount of the carrier gas/sample combination which passes through the column (18). As the pressure of the carrier gas in the column (18) is controlled by operation of the valve (34), the carrier gas flow rate is also controlled.

Depending upon the particular choice of detector (30), the preferred embodiments may also include means for providing support gas to the detector. It will be appreciated that the support gas may comprise one or more component gasses—such as, for example, hydrogen, nitrogen, helium, air, or oxygen-depending upon the detector employed. The pressure of the support gas entering the .detector (30) is sensed by a transducer (38) to provide another signal representative of that operating condition parameter to the interface (42) and processor (40). The pressure of the support gas is then controlled by a valve (36) in response to an appropriate signal through the interface (42) from the processor (40). Suitable support gas sources, valves, and transducers, along with related apparatus not shown, may be selected as known in the art.

Figure 4:
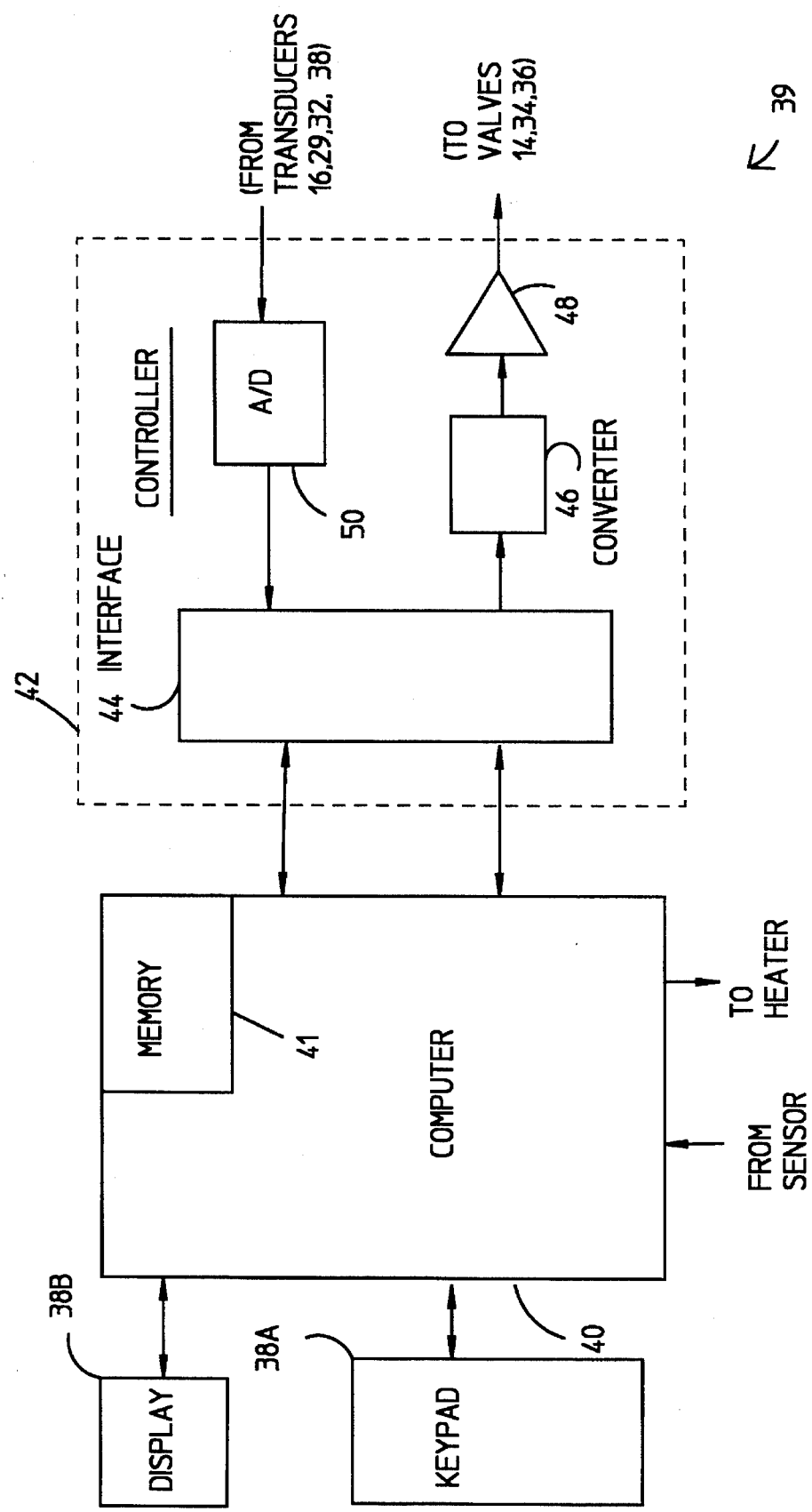
FIG. 4 is a simplified schematic representation of an electronic pressure controller featured in the system illustrated in FIGS. 2 or 3.

Turning now to FIG. 4, the fluid flow control in the chromatographic system (10A, 10B) will now be described in greater detail. The processor (40) may be selected from computing devices amenable to the practice of this invention, e.g., one or more computing devices such computers, microprocessors, microcontrollers, switches, logic gates, or any equivalent logic device capable of performing the computations described hereinbelow. Processor (40) preferably is coupled with an information input means (38A) preferably in the form of a keyboard, keypad, or computer mouse, or another processor (not shown), for inputting additional operating condition parameters, system calibration data, and the like. Information output means (38B) such as an alphanumeric or video display or printer may also be utilized. The preferred processor (40) may further include memory (41) in the form of volatile and non-volatile storage devices in which input and output information, operating condition parameters, system information, and programs can be stored and retrieved. Operating commands, device and fluid type information, detector response attributes, column temperature programs, and other information necessary to perform a chromatographic analysis may be entered into the processor (40) by way of the input means (38) or retrieved from memory (41). Messages prompting the user to enter certain information, such as a desired operating parameter e.g., inlet pressure or linear fluid flow in the column, can be generated by the processor (40) and displayed on the display (38B). The processor (40) may further comprise network and bus system (input/output or I/O) controllers, isolation devices, clocks, and other related electronic components for performing control, processing, and communication tasks other than those described herein.

Another function of the processor (40) is to control the temperature of the oven (24). To do so, the processor (40) transmits a control signal to the heater (26) to increase or decrease the amount of heat transferred from the heater to the oven (24). The sensor (28) senses the temperature in the oven (24) and transmits a feedback signal representative of such temperature to the processor (40). By monitoring the temperature feedback signal from the sensor (28), the processor (40) can maintain the temperature in the oven (24) at a desired level by controlling the heater (26). The present invention contemplates the control of the oven temperature according to computations described hereinbelow with respect to FIGS. 5–7.

In a particular feature of the invention, it will be appreciated that the flow controllers illustrated in FIGS. 2 and 3 (in the form of valves (14, 34, 36) are made to open or close to maintain one or more desired system operating condition parameters that have been entered by the system operator on the keypad (38) or retrieved from memory (41), As illustrated in FIG. 4, the preferred embodiment includes an electronic pressure control (EPC) system (39) for accurate and repeatable control of the fluid flow to the column (18). The active electronic pressure control preferably effects active control of the operation of the valves (14, 34, 36) so as to control both the inlet pressure and the flow rate of the carrier fluid. The processor (40) generates appropriate control signals from interface (44) to causes one or more valves to increase or decrease the pressure or flow rate of the fluid passing therethrough. For example, valve (14) in FIG. 2 may be operated via the open time of an orifice (in the case of a modulating control valve) or the height of the gap over an orifice area (in the case of a proportional control valve) to regulate the inlet pressure of the carrier fluid provided to the separation column (18). The fluid flow control in the forward regulated system shown in FIG. 2 may thus be achieved according to, inter alia, the pressure sensed by pressure sensor (16) located downstream from the control valve (14). A rise in the sensed pressure causes the pressure sensor output signal (preferably, a voltage) to rise. This voltage is transmitted via cabling to the EPC system (39). In response, a new and slightly lower control voltage is fed back to the control valve (14) from the interface (42) according to computations accomplished by the processor (40). The gap in the control valve will then be reduced slightly, resulting in a slightly smaller flow through the valve and a slightly lower pressure at the pressure sensor. This feedback process occurs at relatively high frequency, resulting in very smooth and repeatable pressure control.

As mentioned above, certain desired system operating condition parameters, preferably the desired inlet pressure, may be entered by the operator by digital entry at the keyboard (38) or through another controlling data system; actual operating system parameters are sensed and provided to the processor for use in computations. In accordance with a particular feature of the invention, barometric pressure $p_{atm}$ is considered one such actual operating condition parameter to be sensed with the absolute pressure sensor (29), such that a value representative of that parameter is then used in computations performed by the EPC system to derive control signals for effecting inlet pressure changes. The processor (40) can maintain the inlet pressure at a computed level according to control loop firmware resident in memory (41) by generating control signals that direct the operation of the valve (14). The generated control signals are in a digital form and may be provided to the valve (14) or converted to analog form by a digital to analog (D/A) converter (46) and appropriately amplified by an amplifier (48) prior to transmission to the valve (14). Depending upon the character of the sense signals (whether analog or digital), analog sense signals from the transducers may be provided to the processor (40) by first converting the analog signals generated by the pressure transducers (16) from analog to a digital signal by a multichannel analog to digital (A/D) converter (50). Digital signals generated by the A/D converter are then supplied to the processor (40). Digital sense signals may be passed directly to the processor (40). Further details on the selection and operation of components such as the converters (46, 50), processor (40), interface (44), and transducers (16, 29, 32) may be devised according to control system techniques known in the art.

Figure 5:
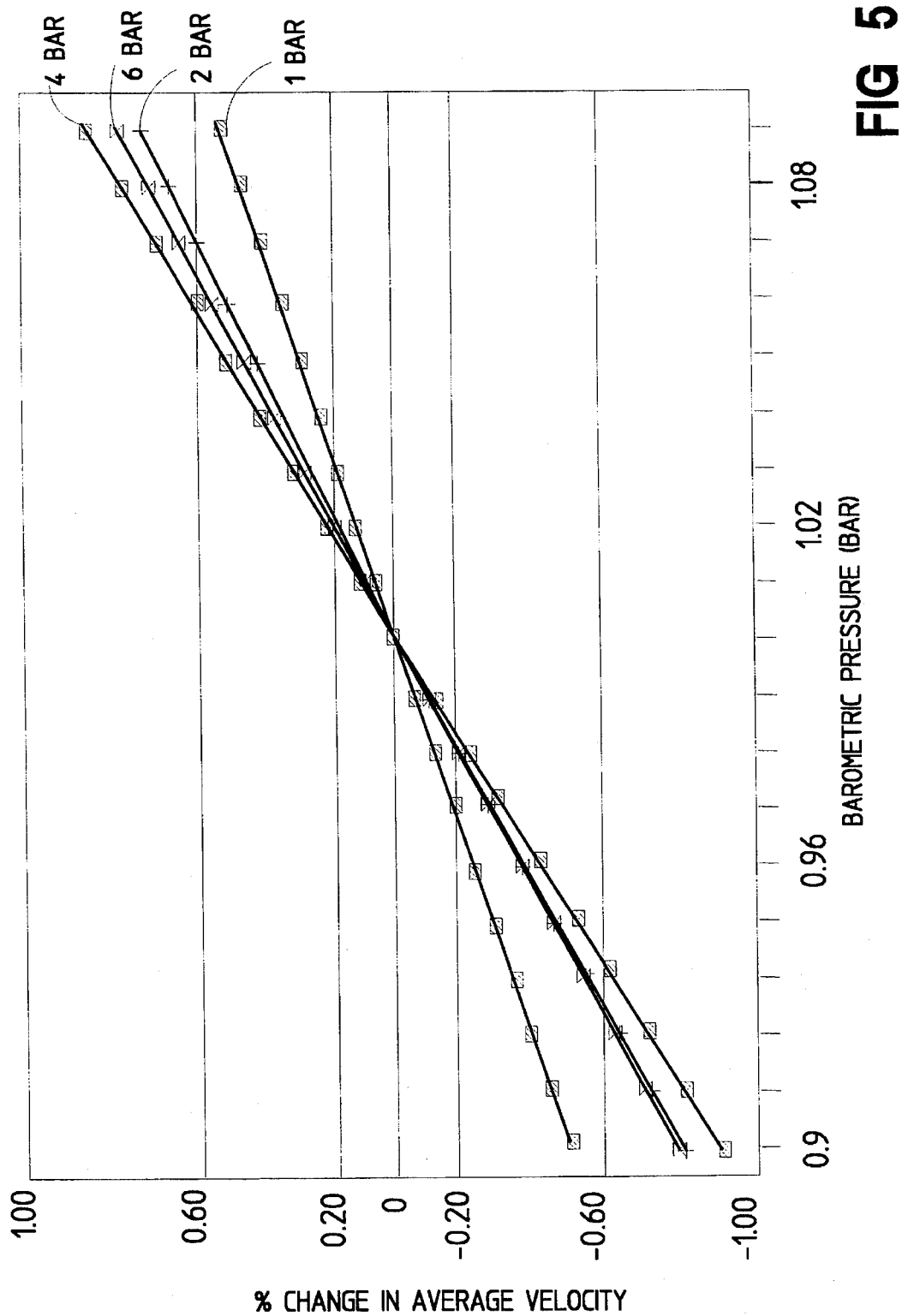
FIG. 5 is a graphical representation of the effect of variation in barometric pressure on the average linear velocity of a column fluid flow, wherein the effect of barometric pressure variation is not compensated according to the teachings of the present invention.

Turning now to FIGS. 5 and 6, it will be appreciated that the equations that govern flow through a column must be based on absolute (not gauge) pressures. Hence, and according to the present invention, retention time stability may be considered a function of the column fluid flow, and thus a function of actual operating condition parameters such as the column temperature, inlet pressure, and outlet pressure. Moreover, these operating condition parameters are capable of differentiation to find the effect of each parameter on the retention time.

In the particular feedback control system described hereinabove, the processor (40) receives one or more desired operating condition parameters in the form of the desired inlet pressure, the desired column mass flow setpoint, or the desired column average linear velocity. Other operating condition parameters representative of other data associated with the operation of the system (10A, 10B), such as, gas type and column dimensions, may be retrieved from memory (41). After determining the desired average linear velocity of the carrier gas at a selected desired operating condition parameter, such as the desired column inlet pressure referenced to normalized temperature and pressure, the result is held as a 'reference' for comparison to the results of subsequent calculations. Finally, by computing one or more new operating condition parameters (such as inlet pressure) that will adjust the actual average linear velocity to the desired average linear velocity, the appropriate operating condition parameter(s) can be adjusted. As an intermediate result of such control, the desired average linear velocity is realized in actuality, and thus made constant. The subsequent result of realizing the desired average linear velocity, however, is to stabilize the retention time of the system (10A, 10B) even while the system is influenced by variations in barometric pressure $p_{atm}$. The present invention contemplates the use of one or more desired operating condition parameters, preferably in the form of the desired inlet pressure, the desired column flow, or the desired column average linear velocity, as being determinative of the desired average linear flow of the carrier fluid. In the calculations to follow, the desired inlet pressure has been selected as the desired operating condition parameter. However, a selection of inlet pressure should not be considered limiting, as other operating condition parameters may be selected for use in the following computations.

To calculate a value for the average linear velocity of fluid flow in a given separation column, the linear velocity of the column flow at the column outlet $\mu_o$ is related to the column inlet and outlet pressures by:

$$u_o = \left( \frac{F_{c(o)}}{60\pi r^2} \right) = \left( \frac{r^2(p_i^2 - p_o^2)}{16 \eta L p_o} \right) \qquad (1)$$

where $F_{c(o)}$ is the outlet volumetric flow rate, $\eta$ is the viscosity, $p_i$ and $p_o$ are the column inlet and outlet pressures, and r and L are the column radius and length, respectively. The average linear velocity $\bar{\mu}$, is related to the outlet linear velocity by a correction factor, j:

$$\bar{\mu} = \mu_o \times j \qquad (2)$$

$$j = \frac{3(P^2 - 1)}{2(P^3 - 1)} \text{ where } P = \frac{p_i}{p_o} \qquad (3)$$

hence $$j = \frac{3 p_o (p_i^2 - p_o^2)}{2(p_i^3 - p_o^3)} \qquad (4)$$

and combining the equations for average linear velocity and outlet velocity, $$\bar{u} = \left( \frac{3 r^2}{32 \eta L} \right) \left( \frac{(p_i^2 - p_o^2)^2}{(p_i^3 - p_o^3)} \right) \qquad (5)$$

where $p_i$ is the absolute inlet pressure, $p_o$ is the outlet pressure, $\eta$ is the viscosity coefficient of the gas, L is the length of the column, and r is column internal radius.

One may now appreciate that the contemplated electronic pressure control system may be programmed to perform calculations based on the foregoing definition of the average linear velocity of the fluid flow in the separation column. As will be seen below, the preferred embodiment performs calculations that relate two differing interpretations of the average linear velocity as defined above. First, there is the desired average linear velocity of the fluid being controlled; secondly, there is the actual average linear velocity of the fluid being controlled. Further, as the system operator is expected to enter the desired gauge pressure $p_{gd}$ as a desired operating condition parameter, one may consider $p_{gd} + p_{atm} = p_i$ and at nominal operation, $p_{atm} = p_o$.

Accordingly, the desired average linear velocity may be defined as:

$$\bar{u}_{ref} = \frac{3 r^2}{32 \eta L} \frac{(p_{id}^2 - p_{o1atm}^2)^2}{(p_{id}^3 - p_{o1atm}^3)} \qquad (6)$$

where $p_{id}$=the inlet pressure provided as a desired operating condition parameter and $p_{o1atm}$=1 atmosphere. The actual average linear velocity may be defined as:

$$\bar{u}_{actual} = \frac{3 r^2}{32 \eta L} \frac{(p_i^2 - p_{or}^2)^2}{(p_i^3 - p_{or}^3)} \qquad (7)$$

where $p_i = p_g + p_{or}$ and $p_{or}$=the sensed barometric pressure (which is subject to variation.) The object of the fluid flow control is to achieve a desired relationship between $\mu_{ref}$ and $\mu_{actual}$ that is defined as:

$$\mu_{ref} = \mu_{actual}$$

Combining and simplifying equations (6)–(8) we arrive at the desired relationship:

$$\frac{(p_{id}^2 - p_{o1atm}^2)^2}{(p_{id}^3 - p_{o1atm}^3)} = \frac{(p_i^2 - p_{or}^2)^2}{(p_i^3 - p_{or}^3)} \qquad (9)$$

where $p_i = p_g + p_{or}$

By solving Equation (9) for $p_g$, one arrives at a corrected value of the inlet pressure that will maintain the actual average linear velocity at a constant value.

In the operation of the preferred embodiment, as $p_{or}$ varies with time, the electronic pressure control accordingly changes $p_g$ so that $\mu_{desired} = \mu_{actual}$, where $\mu_{desired}$ is the value calculated from at least one desired operating parameter (e.g., a value provided as an input by the operator). Such determinations by the processor may be effected according to an embedded program that utilizes the above equations according to computational techniques known in the art. (For example, the requisite determination may be obtained by by retrieving predetermined values from a lookup table. Correction factors can be predetermined such that the value of $p_g$ for a given $p_o$ may be stored in memory 41 for conversion and use by the microprocessor as a correction factor. By doing so, the actual average linear velocity is made constant, with a concomitant improvement in the retention time stability of the chromatographic system.

EXAMPLE

In the contemplated analytical system, the average linear velocity of fluid flow in a separation column is subject to analysis, as shown above, in order to arrive at a correction to the separation column inlet pressure to achieve improved retention time stability. The performance of an experimental version of the preferred embodiment was accordingly modelled in a modified Hewlett Packard HP 5890A to determine the effect of barometric pressure changes on retention time, and the results are indicated in FIGS. 5 and 6.

FIG. 5 illustrates the effect of barometric pressure on the actual average linear velocity of a typical capillary column under test. FIG. 6 exemplifies computed, experimental correction factors for the variation in a given inlet pressure in a typical capillary column under test. The illustrated factors were computed to produce a constant average column velocity, relative to 1 bar outlet pressure, for various inlet pressures. FIG. 6 shows the correction factors as column pressure in mpsi for a 0.2 psi range of variation in barometric pressure. For example, at a column head pressure of 3 bar and an initial barometric pressure of 0.9 bar, a barometric change of 0.2 psi (a reduction of 1.1 bar to 0.9 bar) would require a correction to the column head pressure of 63.5 mpsi. It is notable that the correction factor is shown to be larger for higher inlet pressures in comparison to the correction factor for lower inlet pressures. FIGS. 5 and 6 thus indicate that the effect of a barometric pressure variation on the performance of the analytical system becomes greater at higher inlet pressures. This is an important factor when the allowable inlet pressure is increased, as may be found in gas chromatographic analytical systems that depend upon greatly elevated inlet pressures to achieve what is known as "high-speed" chromatography.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for performing a chromatographic analysis of a fluid in a separation column having an outlet subject to a barometric pressure $p_{atm}$, comprising the steps of:

providing fluid flow of the fluid in the separation column;

sensing a plurality of actual operating condition parameters to which the fluid flow is subjected, the plurality including the barometric pressure $p_{atm}$;

providing information representative of a desired operating condition parameter;

determining a desired average linear velocity of the fluid flow according to the desired operating system parameter;

determining an actual average linear velocity of the fluid flow according to the sensed plurality of actual operating condition parameters; and controlling, as a function of a predetermined relationship of the desired average linear velocity to the actual average linear velocity, the amount of fluid flow to cause the actual average linear velocity to substantially equal the desired average linear velocity.

2. The method of claim 1, wherein the information representative of a desired operation condition parameter includes data representative of desired inlet pressure ($p_i$).

3. The method of claim 1, wherein the information representative of a desired operating condition parameter includes data representative of a fluid flow rate.

4. The method of claim 1, wherein the information representative of a desired operation condition parameter includes data representative of a desired average linear velocity of the fluid at the column outlet ($\mu_o$).

5. The method of claim 1, wherein the fluid flow control is provided by a signal-controlled inlet pressure valve, and the step of controlling the fluid flow further comprises computing an adjusted inlet pressure that will adjust the actual average linear velocity to the desired average linear velocity, and further comprising the step of applying a control signal representative of the adjusted inlet pressure to the inlet pressure valve.

6. The method of claim 1, wherein the fluid flow control is provided by a signal-controlled volumetric flow controller, and the step of determining an adjustment to the fluid flow further comprises computing an adjusted volumetric flow rate that will adjust the actual average linear velocity to the desired average linear velocity, and further comprising the step of applying a control signal representative of the adjusted volumetric flow rate to the flow controller.

7. The method of claim 1, wherein the step of determining the actual average linear velocity is performed in accordance with an actual operating condition parameter selected from the following group:

Tc=Column Temperature (Absolute Temperature),

Ts=Standard Ambient Temperature (Absolute Temperature),

Ps=Standard Ambient Pressure (referenced to 1 atm=760 torr), d=Column diameter,

L=Column length, $p_i$=Inlet Pressure, $p_o$=Outlet Pressure, $\mu_o$=Linear velocity of fluid at column outlet, $\mu$=Average linear velocity of fluid, $F_{co}$ =column volumetric flow $\eta$=Fluid Viscosity.

8. The method of claim 1, wherein the relationship is provided according to the formula:

$$\mu_{ref} = \mu_{actual} \qquad (8)$$

wherein $\mu_{ref}$=desired average linear velocity, and $\mu_{actual}$=the actual average linear velocity, respectively, of the fluid flow.

9. The method of claim 8, wherein the fluid comprises a carrier gas.

10. The method of claim 8, wherein the step of sensing a plurality of operating condition parameters includes receiving a first sense signal representative of the separation column inlet pressure $p_i$ and a second sense signal representative of the separation column outlet pressure $p_o$.

11. The method of claim 10, wherein the step of sensing a plurality of operating condition parameters includes referencing one of the first sense signal and the second sense signal to a signal representative of the ambient barometric pressure $p_{atm}$.

12. The method of claim 9, wherein the relationship is provided according to the formula:

$$\frac{(p_{id}^2 - p_{olatm}^2)^2}{(p_{id}^3 - p_{olatm}^3)} = \frac{(p_i^2 - p_{or}^2)^2}{(p_i^3 - p_{or}^3)}$$

where: $p_i$ is the absolute inlet pressure, $p_{id}$ is the inlet pressure provided as a desired operating condition parameter, $p_o$ is the outlet pressure, $p_{or}$ is the sensed barometric pressure, $p_{gd}$ is the desired gauge pressure as a desired operating condition parameter, and $p_{olatm}$ is the outlet pressure at 1 atmosphere.

13. The method of claim 9, further comprising the steps of:

providing the fluid flow from the separation column outlet to a detector; and combining a support gas with the fluid flow to the detector, wherein the step of sensing a plurality of operating condition parameters includes receiving a third sense signal representative of a detector support gas pressure.

14. The method of claim 9, wherein a sample is injected into said fluid through an injection port, and wherein the flow of said carrier gas is controlled upstream from said injection port.

15. The method of claim 9, wherein a sample is injected into said fluid through an injection port, and wherein the flow of said fluid is controlled downstream from said injection port.

16. Apparatus for performing a chromatographic analysis of a fluid in a separation column having an outlet subject to a barometric pressure $p_{atm}$, comprising:

fluid flow controller for providing a selectable flow of the fluid in the separation column;

a plurality of transducers for sensing a respective plurality of actual operating condition parameters to which the fluid flow is subjected, the plurality including the barometric pressure $p_{atm}$;

means for providing information representative of a desired operating condition parameter;

a processor for:
   a. determining a desired average linear velocity of the fluid flow according to the desired operating system parameter,
   b. determining an actual average linear velocity of the fluid flow according to the sensed plurality of actual operating condition parameters;
   c. determining, as a function of a predetermined relationship of the desired average linear velocity to the actual average linear velocity, the amount of fluid flow to cause the actual average linear velocity to substantially equal the desired average linear velocity; and an interface for providing a control signal representative of the determined fluid flow amount to the fluid flow controller.

17. The apparatus of claim 16, wherein the information providing means further comprises an information input device.

18. The apparatus of claim 16, further comprising an information output device.

19. The apparatus of claim 16, further comprising a memory device for providing a program representing the predetermined relationship of the desired average linear velocity to the actual average linear velocity,.

20. The apparatus of claim 16, wherein the fluid flow controller further comprises an inlet pressure valve, and the determined fluid flow amount further comprises an adjusted inlet pressure.

21. The apparatus of claim 16, wherein the fluid flow controller further comprises a volumetric flow controller, and the determined fluid flow amount further comprises an adjusted volumetric flow rate.

22. The apparatus of claim 16, wherein the fluid comprises a carrier gas.

23. The apparatus of claim 16, wherein the plurality of transducers includes a pressure sensor for providing a first sense signal representative of the separation column inlet pressure $p_i$.

24. The apparatus of claim 23, wherein the plurality of transducers includes a pressure sensor for providing a sense signal representative of the separation column outlet pressure $p_o$.

25. The apparatus of claim 16, wherein the predetermined relationship is provided according to:

$$\mu_{ref} = \mu_{actual} \qquad (8)$$

wherein $\mu_{ref}$=desired average linear velocity, and $\mu_{actual}$=the actual average linear velocity, respectively, of the fluid flow.

26. The apparatus of claim 25, wherein the predetermined relationship is further provided according to:

$$\frac{(p_{id}^2 - p_{olatm}^2)^2}{(p_{id}^3 - p_{olatm}^3)} = \frac{(p_i^2 - p_{or}^2)^2}{(p_i^3 - p_{or}^3)}$$

27. The apparatus of claim 16, further comprising an injection port wherein a sample may be injected into said fluid, and wherein the fluid flow controller is located to control the fluid flow upstream from said injection port.

28. The apparatus of claim 16, further comprising an injection port wherein a sample may be injected into said fluid, and wherein the fluid flow controller is located to control the fluid flow downstream from said injection port.

29. The apparatus of claim 16, further comprising:

detector for receiving the fluid flow from the separation column outlet;

means for combining support gas with the fluid flow to the detector; and pressure sensor for providing a sense signal representative of an actual operating parameter in the form of the detector support gas flow.

* * * * *

UNITED STATES PATENT AND TRADEMARK OFFICE
CERTIFICATE OF CORRECTION

PATENT NO. : 5,476,000
DATED : December 19, 1995
INVENTOR(S) : Henderson et al.

It is certified that error appears in the above-indentified patent and that said Letters Patent is hereby corrected as shown below:

Claim 23, Column 14, lines 4-5, "providing a first sense signal" should read: --providing a sense signal--. Claim 26, Column 14, line 20, after the equation, insert: --where: $p_i$ is the absolute inlet pressure, $p_{id}$ is the inlet pressure provided as a desired operating condition parameter, $p_o$ is the outlet pressure, $p_{or}$ is the sensed barometric pressure, $p_{gd}$ is the desired gauge pressure as a desired operating condition parameter, and $p_{olatm}$ is the outlet pressure at 1 atmosphere.--

Signed and Sealed this

Thirtieth Day of July, 1996

Attest:

BRUCE LEHMAN

Attesting Officer     Commissioner of Patents and Trademarks